United States Patent [19]

Trummer

[11] 4,319,197

[45] Mar. 9, 1982

[54] ECG AMPLIFIER OVERLOAD CONTROL

[75] Inventor: James R. Trummer, Tullahoma, Tenn.

[73] Assignee: Keuffel & Esser Company, Morristown, N.J.

[21] Appl. No.: 112,489

[22] Filed: Jan. 16, 1980

[51] Int. Cl.³ ............................................. H03F 21/00
[52] U.S. Cl. ...................................... 330/11; 330/129; 330/136; 330/279; 330/281
[58] Field of Search ................. 330/11, 156, 129, 136, 330/141, 110, 279, 281; 307/358, 359; 358/34, 171

[56] References Cited

U.S. PATENT DOCUMENTS 4,048,573 9/1977 Evans et al. ..................... 330/136 X Primary Examiner—James B. Mullins
Attorney, Agent, or Firm—Lionel N. White

[57] ABSTRACT

An AC coupled amplifier system is protected from overloading input signals by means of a "bootstrap" circuit which provides a compensation signal substantially matching the overscale portion of such input signal and applies that compensation signal to the coupling capacitor as an offset in order to prevent excessive charge accumulation on that capacitor. A voltage controlled current source serves as a signal range limiter in the circuit and responds to overscale input signals by causing a circuit loop opening and forcing loop closure in a secondary feedback circuit from which the extent of input signal overscale is determined. The matching compensation signal is then derived from such determination. The protection circuit further provides a reset function to account for extended overscale input signal levels.

9 Claims, 5 Drawing Figures

ECG AMPLIFIER OVERLOAD CONTROL

BACKGROUND

The present invention relates to electronic amplifier systems and, in particular, to such a system which is exceptionally well adapted for use in instruments utilized in medical diagnoses and monitoring of physiological functions. This novel amplifier system exhibits the normal condition stability of AC coupling, yet is capable of providing the effective recovery from a broad range of overload conditions which has heretofore been available only with the less desirable DC coupled amplifiers.

Because of their ability to reject undesirable input signal DC components arising, for example, from electrode offset potentials or long term DC drifts, AC coupled amplifiers are employed for virtually all routine diagnostic and monitoring applications involving the measurement of electrical potentials associated with the human heart. However, in order to faithfully reproduce these electrical signals, the time constants associated with the AC coupling capacitors in the signal processing amplifier must be relatively long. For example, time constants which yield a low frequency 3 dB point between about 0.5 Hz and 0.05 Hz are commonly used in ECG monitoring and routine diagnostic ECG equipments.

Unfortunately, the use of such long time constants can result in undesirable amplifier response should the amplifier be driven into overload. Such amplifier overload response may vary from disturbances of the normal signal which severely limit its clinical usefulness to complete loss of the normal signal for several seconds. In addition, these undesired responses may cause malfunctions in additional processing circuitry such as heart rate meters, alarm sensing circuits, signal display scopes, and hard copy recorders.

In actual practice, ECG amplifiers are quite frequently driven into overload conditions. Signals which produce amplifier overload can be broadly classified into two groups; the short, transient type such as may arise from a pacemaker pulse or defibrillator discharge, or the longer term, extended type which may result from electrode recovery following a defibrillator discharge or the presence of a sustained overscale electrode offset potential. Whichever the type, it is evident that the disturbance of the charge on the AC coupling capacitor of the amplifier from its nominal value by the overload signal is the primary factor which results in the undesired residual amplifier response after the overload signal passes.

Previously available amplifier systems have been generally designed to deal with the two broad classes of overload signals by means of distinctly different circuitry, each optimized to handle separately one or the other class of overload signal. More specifically, signal overloads of a short or transient nature have usually been processed through slew rate limiter circuits which limit the amount of charge disturbance on the coupling capacitor by controlling the maximum rate of change at which charge can be either increased or decreased in the capacitor. Signal overloads of a longer duration have normally been dealt with by various circuit means which either modify coupling time constants or provide controlled charge establishment on the coupling capacitor after a specific interval of time.

While slew rate limiting is an effective means for suppressing transient disturbances, it has various inherent disadvantages which restrict its utility. For example, slew rate limiting forces a compromise between the high frequency signal handling ability of the amplifier and the amount of transient suppression desired. This represents a definite disadvantage, since reproduction of the higher frequency components is desirable for certain clinically encountered heart potentials such as large amplitude, rapidly changing signals associated with pediatric patients, neonatal patients, and certain invasive measurements on adult patients.

Further, since the rate of change in decreasing signal level is no less affected, slew rate limiting produces a stretching effect for pulse type overloads which essentially doubles the width of pacemaker "spikes" and aggravates the problem of distinguishing in heart rate meter circuits between such a "spike" and certain narrow QRS complexes in adults.

In addition, if slew rate limiting is applied to the degree necessary to suppress to a negligible level any baseline disturbance of the normal ECG signal, a pacemaker "spike" is so suppressed that it is difficult to determine the temporal relationship between the "spike" and the ECG signal. The ability to "see" the pacemaker "spike" without undue disturbance of the normal ECG signal or the heart rate counting circuitry is particularly important for diagnostic procedures and research studies such as pacemaker-cardiac capture mechanisms or certain high rate atrial pacing techniques.

On the other hand, charge re-establishment circuits are severely limited in utility to the specific overload conditions for which they are designed. For example, if the duration of the overload is longer than a brief transient but shorter than the specific time interval in which such a circuit acts to compensate for a charge disturbance, the charge on the coupling capacitor may be disturbed to such an extent that the normal signal is displaced outside the operating range of associated processing apparatus such as display scopes, hard copy recorders, or heart rate meters. When such a condition occurs it can take several seconds for the signal to return to a range where these peripheral devices can provide useful data. Also, such circuits seldom provide well-defined amplifier output response during the period of time the overload persists. As a result of such a lack of defined output level subsequent signal processing circuits can be overloaded. Further lacking are means for controlling charge compensation in proportion to the gain or scale factor chosen by the equipment operator. Such fixed compensation circuitry thus results in much longer recovery times whenever the gain or scale factor of the amplifier is increased.

SUMMARY

The amplifier system of the present invention obviates the noted disadvantages of previous systems by means of a "bootstrap" technique which provides an exact linear replica of that portion of an input signal which exceeds a predetermined constant, and applies that replica of what is in effect an overload signal to the coupling capacitor in such a manner as to oppose the change which would normally occur in the capacitor charge as a result of such overload. Since the predetermined constant is preferably selected to be equal to the nominal full scale range of the system, an otherwise overloading signal appears to the coupling capacitor as not more than a nominal full scale signal regardless of amplitude, wave shape, or duration. As a result, the time constant associated with the coupling capacitor may be sufficiently large to ensure proper signal reproduction without fear of deleterious amplifier response to overloading input signals.

The system comprises as a key element an operational transconductance amplifier (OTA) which operates as a voltage controlled current source with a preset maximum symmetrical output current which essentially establishes the desired nominal full scale range. Under normal signal conditions, i.e. where the input signal is less than that which would result in an amplified overscale output, the OTA continues to supply current to a variable resistor network load within the system and amplified signal output continues unhindered. With the occurrence of an overloading input, however, the current output of the OTA increases to its predetermined limit at which point it is abruptly clamped forcing a loop closure in associated elements with a resulting feedback of the excessive input to counter the charge buildup in the AC coupling capacitor.

Further, variable load for the OTA is arranged to change in response to any operator-selected change in the gain or scale factor of the system in order to ensure capacitor charge compensation which is proportional to amplifier gain. Thus, whenever the scale factor is increased, for example, the OTA load is appropriately decreased to an extent sufficient to cause the maximum current output to occur at a lower input signal level with the result that loop closure and feedback to the coupling capacitor are effected soon enough to avoid overscale output.

In addition to the noted "bootstrap" feedback protection of the coupling capacitor during short term overload conditions, the amplifier system also includes means for preventing disruptive capacitor charge disturbance which would otherwise result from overloads of extended duration. To this end means including a "window" circuit is utilized to detect the existence of an overload and control the application of a reset signal to modify the capacitor charge and shift the output signal to a level within the desired range. This detector means further includes a delay function which ensures the distinction between transient overload input signals for which compensation is provided in the "bootstrap" circuitry and long duration overloads, such as arise from electrosurgical procedures, for which reset capability is desirable to prevent amplifier saturation.

The instant invention thus provides an amplifier system which protects the AC coupling capacitor from exposure to signals greater than nominal full scale regardless of input overload conditions, yet provides precisely defined output levels under such conditions and, in addition, ensures the accurate retention of essential data following short term overload signals. As a result, the utility of clinical ECG instrumentation, for example, has been considerably expanded to the extent that such equipment may be universally employed in substantially all conditions of physiological monitoring and diagnostics.

DRAWINGS

DESCRIPTION

Figure 1:
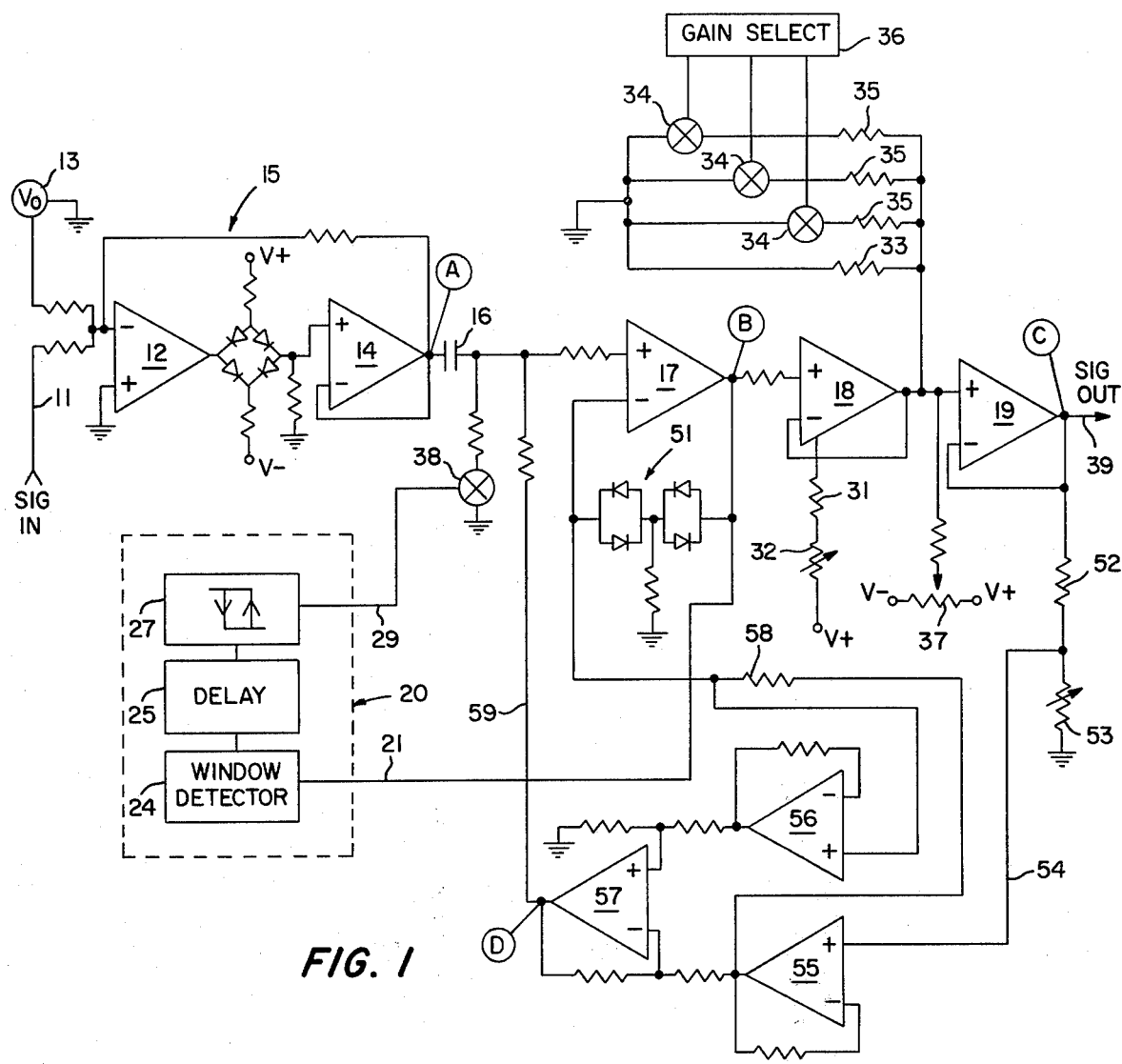
FIG. 1 is a schematic diagram of a preferred embodiment of an amplifier according to the present invention.

Referring to the schematic diagram of FIG. 1, an input signal, such as an ECG signal which has been partially processed and amplified in the usual manner by common means, not shown, is carried on conductor 11 to be summed with the reference voltage $V_o$ from precision source 13 in summing amplifier/DC limiter 15 comprising operational amplifiers 12,14. Amplifier/limiter 15 has a normal signal gain of unity and provides bipolar limiting points of about one third the ±15 V supply voltage used in the system. The preamplified signal introduced to the "bootstrap" circuitry via coupling capacitor 16 is thus restricted to a dynamic range of about 10 V peak-to-peak.

A fivefold operating voltage gain in the signal, as set by the division ratio of resistors 52,53, is effected in the non-inverting circuit comprising amplifier elements 17,18, and 19. Device 17 is an FET input operational amplifier with low input bias currents and offset voltage, such as a PMI OP-15; and op amp 19, e.g. a PMI OP-11, is used as a non-inverting, unity gain buffer. The limiting element of the system is operational transconductance amplifier 18, such as an RCA CA 3080, which operates as a unity gain voltage controlled current source having a maximum symmetrical output current which may be readily established by means of the bias controlled at resistors 31,32. Any slight asymmetry in the current output from OTA 18 may be compensated at variable resistor 37.

Resistor 33 serves as a load for the current output of OTA 18 and determines the input voltage level at which the maximum current output level is reached. Additional resistors 35 introduced into a parallel network with resistor 33 by means of solid state switches 34 provide a means for varying the load and thus automatically ensuring coupling capacitor charge compensation which is proportional to any changes in scale factor of the system effected by the operator at gain selector means 36.

Figures 3, 4, 5:
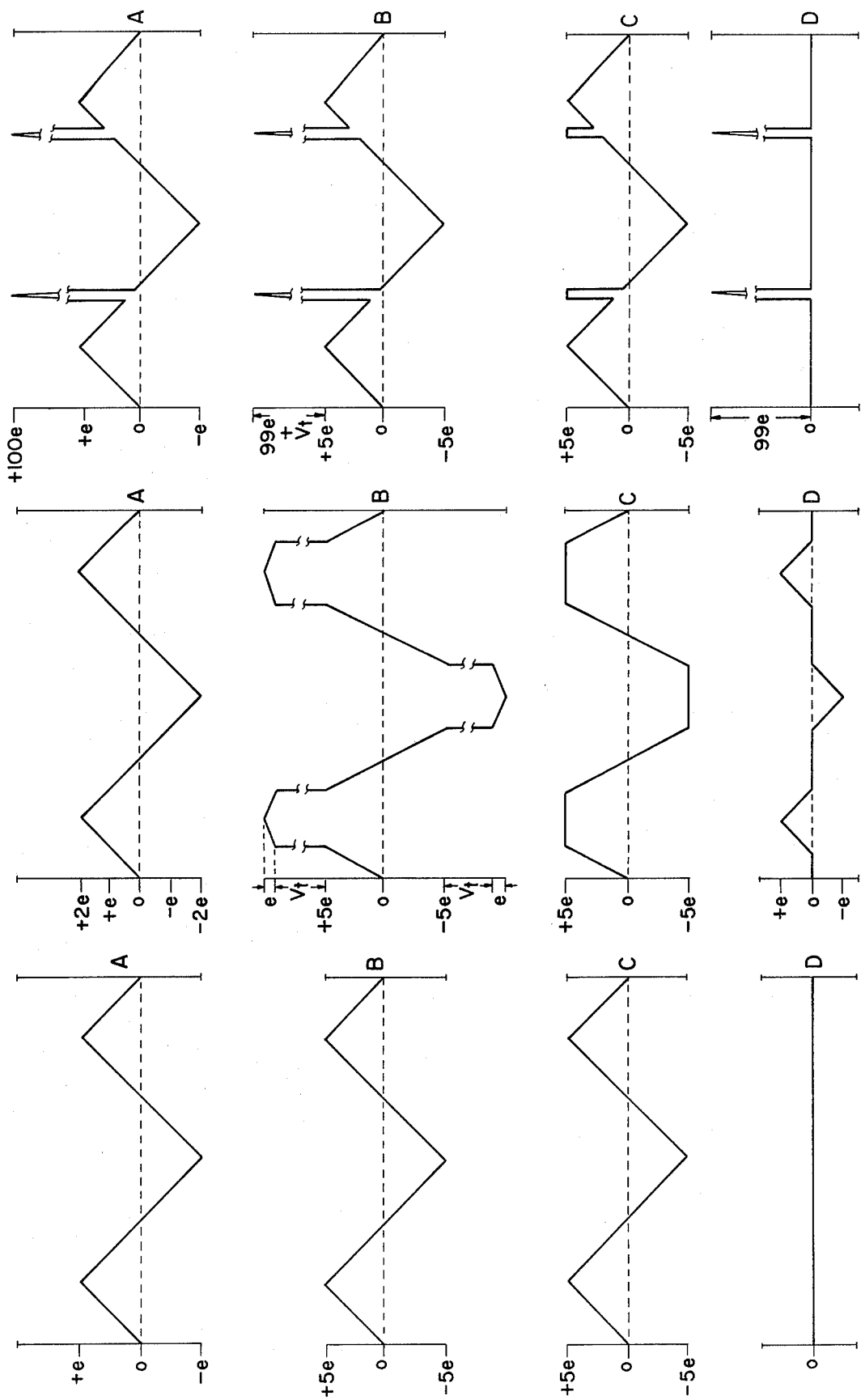
FIG. 3 depicts representative waveforms at indicated test points throughout the amplifier of FIG. 1 during the processing of a normal full scale signal.
FIG. 4 depicts such representative waveforms during the processing of a relatively long term overscale signal.
FIG. 5 depicts such representative waveforms during the processing of a shot term, "spike"-type overscale signal.

Under normal operating conditions, i.e. where all signal levels are within nominal full scale range, OTA 18 can continue to supply current to its load and, as a result, its output voltage tracks the signal input from op amp 17 and is buffered at op amp 19 to produce the amplified output signal which proceeds to further processing for visual display and the like in peripheral equipment, not shown. Signal waveforms under these conditions are simply represented in FIG. 3 which shows, at A, the preamplified signal at test point A of FIG. 1 as it is input at coupling capacitor 16. As can be seen, this input signal varies within the full load amplitude range of ±e, about ±30 mV. This normal input signal is amplified by a factor of five and appears, as shown at FIG. 3B and 3C, at test points B and C as a ±5e full scale range output signal.

Also comprising the instant overload control system are operational amplifiers 55, 56, 57 which form a precision instrumentation amplifier having a fixed differential voltage gain of unity. By virtue of the division ratio of resistors 52, 53, signal input to this amplifier assembly via conductor 54 is essentially 20% of the output signal appearing at C, thus varying over the full load range of ±e under the normal conditions presently being considered. Further comprising this system is nonlinear network 51 which allows substantially no significant feedback to op amp 17 as long as the signal level at B is less than the network threshold of about 1.2V. Thus, under the present normal operating conditions, there is no voltage difference across resistor 58 and, since the inputs to op amps 55,56 are equal, the resulting output from differential amplifier 57 is zero, as shown at FIG. 3D, and there is no compensating signal potential applied through conductor 59 to the downstream side of coupling capacitor 16. Such a potential is, of course, unnecessary since the input signal is within the nominal full scale range of ±e and can readily be accounted for.

Upon the occurrence of an overload input signal, such as that depicted at FIG. 4A as having an amplitude range of ±2e, i.e. twice the maximum full scale range of the system, the amplified output of op amp 17 at first rises, as shown in FIG. 4B, to a level of ±5e at which, as input thereto, it initiates the maximum current output from OTA 18. At that point the voltage output of OTA 18 is clamped at a level of ±5e, as indicated at the buffered output shown in FIG. 4C, and the resulting substantially infinite gain exhibited by amplifier 17 causes an immediate rise in output potential (point B) which exceeds the threshold ($V_t$ in FIG. 4B) of network 51 and forces loop closure through that network with feedback to device 17, causing op amp 17 thereafter to respond as a unity gain voltage follower of the signal at its input.

As that signal-following voltage change, essentially the signal portion, e, of the input signal in excess of maximum normal input, e, feeds back through network 51 there results a potential difference across resistor 58 which appears at the output (point D) of differential amplifier 57 as a replica of the overloading signal portion, as depicted in FIG. 4D. This replica signal is applied through conductor 59 to coupling capacitor 16 to effectively offset that matching portion of the overload signal input at A which would otherwise be in excess of normal full range.

As soon as the input to op amp 17, and the resulting input to OTA 18, returns to a level within full load range the system returns to normal amplification, as depicted in FIG. 4, with subsequent overloads being similarly accounted for, as shown. In this manner the signal output at C is never allowed to exceed the predetermined full scale range, and the coupling capacitor is prevented from becoming charged to such an extent that recovery from an overloading input and faithful reproduction of otherwise normal input signals are hindered.

In a similar manner, extreme, short term signal overloads in the amplitude range, for example, of 100e, such as might result from cardiac pacemaker pulses (FIG. 5A), are effectively accounted for by the generation of overload replica offset signals (FIG. 5D) which prevent deleterious charge accumulation on the AC coupling capacitor. A particular advantage of the present system is apparent in FIG. 5C which shows the effect of the clamping of the output of OTA 18 to retain the initial, in-scale portion of the overloading "spikes" and establish, for example, the temporal relationship of the pacemaker pulse to the normal ECG signal. Slew rate limiting techniques could simply suppress the "spike" signal to such an extent as to make it relatively indistinguishable or, at best, expanded to a point where it could provide only limited significant clinical data.

Figure 2:
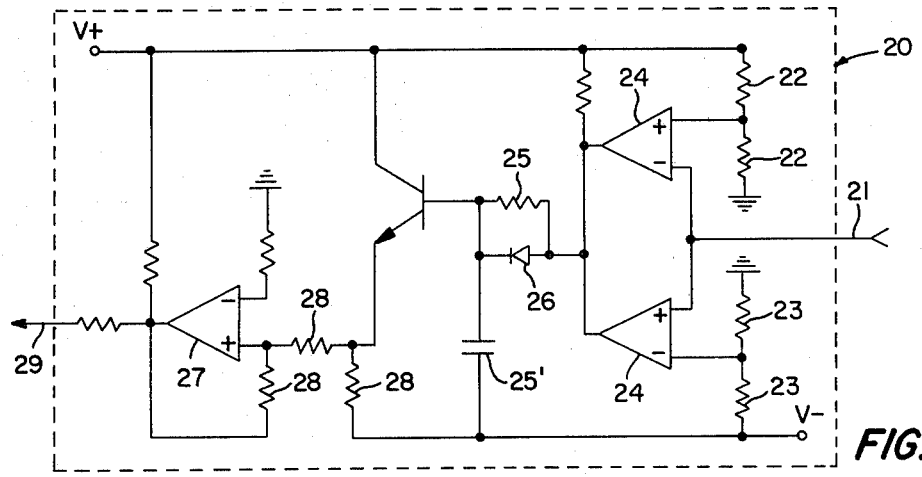
FIG. 2 is a schematic diagram of an overscale detector and reset timing generator comprising the embodiment of FIG. 1.

While the described "bootstrap" feedback circuit provides ample protection against disruptive charge accumulation on the coupling capacitor under overloading signal input conditions, it is often desired that the overscale signal be retained at least to the extent that it may be reproduced in an observable manner, such as an CRT displays. For this purpose the instant system comprises an overscale detector and reset timing generator, generally shown at 20 in FIG. 1 and more specifically depicted in FIG. 2, the purpose of which is to supply a reset pulse which modifies the charge on the coupling capacitor and brings the signal within normal full scale range.

As shown, this assembly comprises a "window" detector which includes comparators 24,24 and preset upper and lower voltage references determined by supply-dividing resistor combinations 22,23. The abrupt and substantial voltage level change in the signal (point B) which is input to the detector circuit on conductor 21 clearly establishes the existence of an overload condition in the system; however, since it is desired that short term overloads such as pacemaker pulses be retained for processing as described, a time delay function comprising RC combination 25,25' is provided to prevent reset for any overload signals which persist for less than an interval of about 420 ms. Sufficiently extended overload signals initiate a reset pulse which is output on conductor 29 to actuate solid state switch 38 and cause modification of the charge on coupling capacitor 16 so as to reduce the extended overload signal, such as generated in electrosurgical devices, to a stable baseline within nominal full scale range.

To ensure a reset pulse of sufficient duration to effectively modify the capacitor charge, comparator 27 and resistors 28 are selected so as to provide a degree of hysteresis which will maintain a reset signal for about 65 ms after termination of the overload signal. In this manner the capacitor charge is allowed sufficient time to return to normal operating levels even in the event of overload signals of marginal duration. Further, in order that repetitive short pulse overload signals not degenerate the noted time delay, diode 26 provides for rapid recharging of capacitor 25', thus effectively reseting the delay function after each short term overload.

The described detector and reset circuitry also provides a reset pulse at occasions of power surge, such as when the ECG system is initially put into operation or when the power supply recovers from momentary interruptions. The output signal is thus retained within full scale range for ultimate display even during such power transitions.

What is claimed is:
1. An overload control circuit for an AC coupled amplifier system comprising:
 (a) voltage-controlled current source means arranged to provide a maximum current output at a voltage input corresponding to a desired full scale signal limit in said amplifier system;
 (b) operational amplifier means for providing said current source input in response to signals input to said amplifier system;

(c) gain control feedback circuit means for said operational amplifier comprising switching means exhibiting a predetermined conductance threshold;

(d) instrumentation amplifier means in circuit with the gain control feedback input of said operational amplifier means and with the output of said amplifier system; said instrumentation amplifier determining the differential between signals appearing at said feedback input and at said system output, and providing a compensation signal corresponding to said differential; and (e) means for applying said compensation signal to the coupling capacitor of said amplifier system, whereby overloading signals input to said system are offset at said capacitor to the extent of signal levels in excess of said full scale limit, thereby preventing excessive charge accumulation on said coupling capacitor.

2. A control circuit according to claim 1 wherein said voltage-controlled current source comprises an operational transconductance amplifier biased to provide said maximum output current.

3. A control circuit according to claim 1 wherein said gain control feedback switching means comprises a substantially symmetrical nonlinear diode network in circuit with the output and the gain control feedback input of said operational amplifier.

4. A control circuit according to claim 1 which further comprises variable load means in circuit with the output of said voltage-controlled current source.

5. A control circuit according to claim 4 wherein said load is automatically varied in response to changes of gain in said amplifier system.

6. A control system according to claim 1 which further comprises reset means in circuit with the output of said operational amplifier for identifying signal excursions at said output indicative of overscale signal input to said amplifier system, and for initiating modification of the charge accumulation on said coupling capacitor due to said overscale input.

7. A control system according to claim 6 wherein said reset means comprises a window detector circuit which provides a reset-initiating signal pulse in response to the input thereto of a signal level in excess of the window reference limits thereof.

8. A control system according to claim 7 wherein said reset means further comprises means for delaying the generation of said signal pulse for a time sufficient to prevent the activation of said reset function by overscale signals of a duration less than a predetermined minimum time.

9. A control system according to claim 8 wherein said reset means further comprises means for extending the duration of said reset-initiating pulse for a time sufficient to ensure the desired coupling capacitor charge modification.

* * * * *